United States Patent
Yu et al.

(10) Patent No.: US 10,302,593 B2
(45) Date of Patent: May 28, 2019

(54) METHOD FOR DETECTING DEFECT OF PIPE, DEVICE FOR DETECTING DEFECT OF PIPE, APPARATUS FOR DETECTING DEFECT OF PIPE

(71) Applicant: NINGBO YINZHOU CITAL ELECTRONIC TECHNOLOGY CO., LTD., Ningbo, Zhejiang (CN)

(72) Inventors: Runqiao Yu, Ningbo (CN); Bin Zhang, Ningbo (CN); Bo Hu, Ningbo (CN); Guisuo Xia, Ningbo (CN); Dongfang Cheng, Ningbo (CN); Qiangqiang Cheng, Ningbo (CN)

(73) Assignee: NINGBO YINZHOU CITAL ELECTRONIC TECHNOLOGY CO., LTD., Ningbo, Zhejiang (CN)

( * ) Notice: Subject to any disclaimer, the term of this patent is extended or adjusted under 35 U.S.C. 154(b) by 23 days.

(21) Appl. No.: 15/124,351

(22) PCT Filed: Jun. 12, 2016

(86) PCT No.: PCT/CN2016/085425
§ 371 (c)(1),
(2) Date: Sep. 7, 2016

(87) PCT Pub. No.: WO2016/197972
PCT Pub. Date: Dec. 15, 2016

(65) Prior Publication Data
US 2017/0176390 A1 Jun. 22, 2017

(51) Int. Cl.
*G01N 27/82* (2006.01)

(52) U.S. Cl.
CPC .................................. *G01N 27/82* (2013.01)

(58) Field of Classification Search
CPC ............................. G01N 27/82; G01N 27/902
See application file for complete search history.

(56) References Cited

U.S. PATENT DOCUMENTS

| | | | |
|---|---|---|---|
| 2003/0011363 A1* | 1/2003 | Wayman | G01N 27/82 324/238 |
| 2003/0169035 A1* | 9/2003 | Crouzen | G01B 7/28 324/230 |
| 2016/0274060 A1* | 9/2016 | Denenberg | G01N 27/9046 |

* cited by examiner

Primary Examiner — Noam Reisner
(74) Attorney, Agent, or Firm — Raymond Y. Chan; David and Raymond Patent Firm (57) ABSTRACT

A method for detecting the defect of the pipe includes the steps of: detecting a first parameter related to a magnetic induction intensity along a length direction of the pipe; determining whether the first parameter exceeds a predetermined threshold; determining a position at which the first parameter exceeds the predetermined threshold as the position of the defect of the pipe; and determining a degree of the defect of the pipe based on a numerical value of the first parameter exceeding the predetermined threshold. Through the detecting device, the defect in the pipe is decided based on parameters related to the magnetic induction intensity, the position of the defect of the pipe is determined according to a position at which the parameters are abnormal, and the degree of the defect of the pipe is determined according to numerical values of the parameters which are abnormal.

15 Claims, 6 Drawing Sheets

METHOD FOR DETECTING DEFECT OF PIPE, DEVICE FOR DETECTING DEFECT OF PIPE, APPARATUS FOR DETECTING DEFECT OF PIPE

CROSS REFERENCE OF RELATED APPLICATION

This is a non-provisional application that claims priority to international application number PCT/CN2016/085425, international filing date Jun. 12, 2016, which claims priority to a first Chinese application number CN201510325744.5, filing date Jun. 12, 2015, a second Chinese application number CN201510321540.4, filing date Jun. 12, 2015, and a third Chinese application number CN201510992345.4, filing date Dec. 25, 2015, the entire contents of each of which are expressly incorporated herein by reference.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to a field of detection technique, and in particular to a method for detecting a defect of a pipe, a device for detecting the defect of the pipe and an apparatus for detecting the defect of the pipe.

Description of Related Arts

With advances in science and technology and requirements in industrial production, a range of usage of a transporting pipe becomes increasingly broad. A long distance transporting pipe is a main transporting manner of a production in an industry of petroleum natural gas. And, if the long distance transporting pipe for the petroleum natural gas has a malfunction such as a leakage or the like, it causes pollution in addition to losses of shutdown and salvage. Therefore, how to ensure a safe operation of the existing long distance transporting pipe and new pipe for the petroleum natural gas to reduce a probability of a security accident and implement a intrinsic safety of the operation of the pipe is an urgent affair of ensuring the safe operation of the pipe.

Since the long distance transporting pipe for the petroleum natural gas is buried underground generally, a main working flow of detecting a defect of such buried pipe are still the following steps: excavating, stripping an antisepsis (incubation) layer, detecting, enclosing and backfilling. It is obvious that this is a destructive detecting method, and a representativeness of data detected and a reliability of an evaluating conclusion are affected by numbers of points excavated (sampled) and a distribution range thereof. Therefore, how to detect the buried pipe without excavating and stopping transporting is a problem that deserves an in-depth exploration.

There are many conventional methods of nondestructive detecting including a method of ultrasonic detection, a method of vortices detection and a method of ray detection. The ultrasonic detection is implemented by using information provided by an interaction between an ultrasonic wave and an object, and the ultrasonic wave can propagate in a metal. an deficiency of such method is that an attenuation of the ultrasonic wave in the air is fast, and there needs a propagation medium of the ultrasonic wave, which may be a coupling agent such as oil or water generally at the time of detection, so it is not appropriate for detection of the buried pipe.

The method of ray detection is a method of nondestructive detecting by using a physical effect (for example, a variation of intensity of radiation, scattering or the like) generated by an interaction between ionizing radiation and a subject to detect a discontinuity, a structure or a thickness or the like in a work piece. It is also not appropriate for the detection of the buried pipe.

The method of vortices detection operates according to a principle of electromagnetic induction, so the method of vortices detection can detect a surface defect and a near surface defect of the work piece. A notable feature of the method of vortices detection is functioning to electrically conductive material rather than ferromagnetic material, but an effect of the ferromagnetic material is not good. Secondly, a fineness, a smoothness, a border or the like of the surface of the work piece to be detected has large influence to the vortices, thus, the method of vortices detection is usually used to the detection of non-ferromagnetic work piece such as a copper tube or the like which has relatively regular shape and relatively clean surface. If the buried pipe is a ferromagnetic pipe, the method of vortices detection can't be used. And, the method of vortices detection also needs an exciting source, and it still needs excavating to detect the buried pipe.

A Chinese patent CN102095080A disclosed a method for detecting the buried pipe using a magnetic method without excavating, and its principle is using magnetism that the buried pipe magnetized by an earth magnetic field itself has as the exciting source and using a flux gate sensor having 1 nT of a resolution of magnetic induction intensity to detect the magnetic induction intensity and attenuation amount above a lower side, and continuing detection results downward at the same time, and detecting a quality of the pipe by data processing. However, it does not disclose how to detect the defect of the buried pipe specifically in the disclosure, thus, it can't determine a position of the defect and a magnitude of the defect of the buried pipe.

SUMMARY OF THE PRESENT INVENTION

Technical problem to be solved by the present invention is to overcome the conventional deficiencies, and technical object of the present invention is to provide a method for detecting a defect of a pipe, a device for detecting the defect of the pipe and an apparatus for detecting the defect of the pipe which can detect a position of the defect and a magnitude of the defect in the pipe accurately.

In order to solve the above technical problem, one aspect of the present invention provides the method for detecting the defect of the pipe comprising the steps executed by a computer of: detecting a first parameter related to a magnetic induction intensity along a length direction of the pipe; determining whether the first parameter exceeds a predetermined threshold; determining a position at which the first parameter exceeds the predetermined threshold as the position of the defect of the pipe; and determining a degree of the defect of the pipe based on a numerical value of the first parameter exceeding the predetermined threshold.

In the above-described method for detecting the defect of the pipe, the first parameter is a rate of change in a second direction of a component of the magnetic induction intensity in a first direction in a three-dimensional system of coordinate.

In the above-described method for detecting the defect of the pipe, the first direction is same as the second direction, or the first direction is different from the second direction.

In the above-described method for detecting the defect of the pipe, the method further comprises the steps of determining the degree of the defect of the pipe based on the numerical value of the first parameter exceeding the predetermined threshold specifically includes: determining the magnitude of the defect of the pipe based on an magnitude of the first parameter exceeding the predetermined threshold; and/or determining a length of the defect of the pipe based on a length in which the first parameter exceeds the predetermined threshold continuously.

In the above-described method for detecting the defect of the pipe, the method further comprises a step of drawing a graphical chart of the magnitude of the first parameter versus a distance of the pipe in the length direction.

In the above-described method for detecting the defect of the pipe, the method further comprises the steps of detecting a second parameter related to the magnetic induction intensity along the length direction of the pipe; determining whether the second parameter exceeds the predetermined threshold; determining a position at which the second parameter exceeds the predetermined threshold as the position of the defect of the pipe; and determining the degree of the defect of the pipe based on the numerical value of the second parameter exceeding the predetermined threshold.

In the above-described method for detecting the defect of the pipe, when the position at which the first parameter exceeds the predetermined threshold is same as the position at which the second parameter exceeds the predetermined threshold, the degree of the defect of the pipe is determined based on the numerical value of the first parameter exceeding the predetermined threshold and the numerical value of the second parameter exceeding the predetermined threshold.

In the above-described method for detecting the defect of the pipe, the second parameter is a rate of change in a fourth direction of a component of the magnetic induction intensity in a third direction in the three-dimensional system of coordinate.

In the above-described method for detecting the defect of the pipe, the third direction is same as the fourth direction, or the third direction is different from the fourth direction.

In the above-described method for detecting the defect of the pipe, the first direction, the second direction, the third direction and the fourth direction are one of a x direction, a y direction and a z direction in the three-dimensional system of coordinate.

In the above-described method for detecting the defect of the pipe, the step of determining whether the first parameter exceeds the predetermined threshold specifically comprises the steps of: executing a differential processing on the first parameter; adding a variance of n times to/subtracting the variance of n times from an average value of the magnitude of the first parameter after the differential processing as the predetermined threshold, wherein $1 \leq n \leq 3$; and determining whether the first parameter exceeds the predetermined threshold.

In the above-described method for detecting the defect of the pipe, the step of determining whether the first parameter exceeds the predetermined threshold further comprises the steps of: in case that there is no pipe to be detected, detecting a third parameter related to the magnetic induction intensity along the length direction of the pipe, wherein the third parameter is a parameter which is same as the first parameter; and in the case that the first parameter is larger than the third parameter, optimizing the first parameter with the third parameter, and determining whether the optimized first parameter exceeds the predetermined threshold.

In the above-described method for detecting the defect of the pipe, the method further comprises the step of in addition to the first parameter and the second parameter related to the magnetic induction intensity, further detecting rates of change in three directions x, y and z in the coordinate system of three components $H_x$, $H_y$ and $H_z$ of the magnetic induction intensity in three reference directions in the three-dimensional system of coordinate along the length direction of the pipe respectively, to constitute a magnetic gradient matrix G including 9 elements in total:

$$G = \begin{bmatrix} \partial H_x/\partial x & \partial H_x/\partial y & \partial H_x/\partial z \\ \partial H_y/\partial x & \partial H_y/\partial y & \partial H_y/\partial z \\ \partial H_z/\partial x & \partial H_z/\partial y & \partial H_z/\partial z \end{bmatrix} = \begin{bmatrix} a_{xx} & a_{xv} & a_{xz} \\ a_{vx} & a_{vv} & a_{vz} \\ a_{zx} & a_{zv} & a_{zz} \end{bmatrix}$$

Another aspect of the present invention provides the device for detecting the defect of the pipe comprising: a computer executing the following module: a detecting unit configured to detect a first parameter related to a magnetic induction intensity along a length direction of the pipe, a deciding unit configured to determine whether the first parameter exceeds a predetermined threshold; and a control unit configured to determine a position at which the first parameter exceeds the predetermined threshold as a position of the defect of the pipe, and determining a degree of the defect of the pipe based on a numerical value of the first parameter exceeding the predetermined threshold.

In the above-described device for detecting the defect of the pipe, the first parameter is a rate of change in a second direction of a component of the magnetic induction intensity in a first direction in a three-dimensional system of coordinate.

In the above-described device for detecting the defect of the pipe, the first direction is same as the second direction, or the first direction is different from the second direction.

In the above-described device for detecting the defect of the pipe, the control unit further comprises: a magnitude of defect determining module configured to determine the magnitude of the defect of the pipe based on a magnitude of the first parameter exceeding the predetermined threshold: and/or a length of defect determining module configured to determine a length of the defect of the pipe based on a length in which the first parameter exceeds the predetermined threshold continuously.

In the above-described device for detecting the defect of the pipe, the device further comprises a drawing unit configured to draw a graphical chart of the magnitude of the first parameter versus a distance in the length direction of the pipe based on the first parameter detected by the detecting unit.

In the above-described device for detecting the defect of the pipe, the detecting unit is further configured to detect a second parameter related to the magnetic induction intensity along the length direction of the pipe; the deciding unit is further configured to determine whether the second parameter exceeds the predetermined threshold; and the control unit is further configured to determine a position at which the second parameter exceeds the predetermined threshold as the position of the defect of the pipe, and determine the degree of the defect of the pipe based on a numerical value of the second parameter exceeding the predetermined threshold.

In the above-described device for detecting the defect of the pipe, when the position at which the first parameter exceeds the predetermined threshold is same as the position at which the second parameter exceeds the predetermined threshold, the control unit determines the magnitude of the defect of the pipe based on the numerical value of the first parameter exceeding the predetermined threshold and the numerical value of the second parameter exceeding the predetermined threshold.

In the above-described device for detecting the defect of the pipe, the second parameter is a rate of change in a fourth direction of a component of the magnetic induction intensity in a third direction in the three-dimensional system of coordinate.

In the above-described device for detecting the defect of the pipe, the third direction is same as the fourth direction, or the third direction is different from the fourth direction.

In the above-described device for detecting the defect of the pipe, the first direction, the second direction, the third direction and the fourth direction are one of a x direction, a y direction and a z direction in the three-dimensional system of coordinate.

In the above-described device for detecting the defect of the pipe, the deciding unit further comprises: a differential processing module configured to execute a differential processing on the first parameter; a arithmetic processing module configured to add a variance of n times to/subtract the variance of n times from an average value of the first parameter after the differential processing of the differential processing module as the predetermined threshold, wherein $1 \leq n \leq 3$; and a deciding module configured to determine whether the first parameter exceeds the predetermined threshold.

In the above-described device for detecting the defect of the pipe, the detecting unit is further configured to detect a third parameter related to the magnetic induction intensity along the length direction of the pipe in case that there is no pipe to be detected, wherein the third parameter is a parameter which is same as the first parameter; and the deciding unit is further configured to optimize the first parameter with the third parameter in case that the first parameter is larger than the third parameter, and determine whether the optimized first parameter exceeds the predetermined threshold.

In the above-described device for detecting the defect of the pipe, the detecting unit is further configured to, in addition to the first parameter and the second parameter related to the magnetic induction intensity, further detect rates of change in three directions x, y and z in the coordinate system of three components $H_x$, $H_y$ and $H_z$ of the magnetic induction intensity in three reference directions in the three-dimensional system of coordinate along the length direction of the pipe respectively, to constitute a magnetic gradient matrix G including 9 elements in total:

$$G = \begin{bmatrix} \partial H_x/\partial x & \partial H_x/\partial y & \partial H_x/\partial z \\ \partial H_y/\partial x & \partial H_y/\partial y & \partial H_y/\partial z \\ \partial H_z/\partial x & \partial H_z/\partial y & \partial H_z/\partial z \end{bmatrix} = \begin{bmatrix} a_{xx} & a_{xv} & a_{xz} \\ a_{vx} & a_{vv} & a_{vz} \\ a_{zx} & a_{zv} & a_{zz} \end{bmatrix}$$

In the above-described device for detecting the defect of the pipe, the detecting unit specifically comprises: a first three-components magnetic measuring sensor, a second three-components magnetic measuring sensor arranged symmetrically with a center of the detecting unit to the first three-components magnetic measuring sensor, a third three-components magnetic measuring sensor and a fourth three-components magnetic measuring sensor arranged symmetrically with a center of the detecting unit to the third three-components magnetic measuring sensor, wherein the first, the second, the third and the fourth three-components magnetic measuring sensors are cross-arranged in a plane; and each magnetic measuring sensor in the first, the second, the third and the fourth three-components magnetic measuring sensors calculate a magnetic gradient of a central position of the cross by detecting values of magnetic induction intensity in three reference directions in the three-dimensional system of coordinate thereof, so as to measure the magnetic gradient matrix G at the central position of the cross:

$$G = \begin{bmatrix} \partial H_x/\partial x & \partial H_x/\partial y & \partial H_x/\partial z \\ \partial H_y/\partial x & \partial H_y/\partial y & \partial H_y/\partial z \\ \partial H_z/\partial x & \partial H_z/\partial y & \partial H_z/\partial z \end{bmatrix} = \begin{bmatrix} a_{xx} & a_{xv} & a_{xz} \\ a_{vx} & a_{vv} & a_{vz} \\ a_{zx} & a_{zv} & a_{zz} \end{bmatrix} =$$

$$\begin{bmatrix} \dfrac{B_{1x} - B_{3x}}{\Delta x} & \dfrac{B_{1y} - B_{3y}}{\Delta x} & \dfrac{B_{2x} - B_{0x}}{\Delta z} \\ \dfrac{B_{1y} - B_{3y}}{\Delta x} & -\left(\dfrac{B_{1x} - B_{3x}}{\Delta x} + \dfrac{B_{2z} - B_{0z}}{\Delta z}\right) & \dfrac{B_{2y} - B_{0y}}{\Delta z} \\ \dfrac{B_{1z} - B_{3z}}{\Delta x} & \dfrac{B_{2y} - B_{0y}}{\Delta z} & \dfrac{B_{2z} - B_{0z}}{\Delta z} \end{bmatrix}$$

wherein, $\Delta x$ is a distance between the first three-components magnetic measuring sensor and the second three-components magnetic measuring sensor, $\Delta z$ is a distance between the third three-components magnetic measuring sensor and the fourth three-components magnetic measuring sensor, $B_{1x}$ is a component of the magnetic induction intensity in the x direction measured by the first three-components magnetic measuring sensor, $B_{1y}$ is a component of the magnetic induction intensity in the y direction measured by the first three-components magnetic measuring sensor, $B_{1z}$ is a component of the magnetic induction intensity in the z direction measured by the first three-components magnetic measuring sensor; $B_{2x}$ is a component of the magnetic induction intensity in the x direction measured by the second three-components magnetic measuring sensor, $B_{2y}$ is a component of the magnetic induction intensity in the y direction measured by the second three-components magnetic measuring sensor, $B_{2z}$ is a component of the magnetic induction intensity in the z direction measured by the second three-components magnetic measuring sensor; $B_{0x}$ is a component of the magnetic induction intensity in the x direction measured by the third three-components magnetic measuring sensor, $B_{0y}$ is a component of the magnetic induction intensity in the y direction measured by the third three-components magnetic measuring sensor, $B_{0z}$ is a component of the magnetic induction intensity in the z direction measured by the third three-components magnetic measuring sensor; $B_{3x}$ is a component of the magnetic induction intensity in the x direction measured by the fourth three-components magnetic measuring sensor, $B_{3y}$ a component of the magnetic induction intensity in the y direction measured by the fourth three-components magnetic measuring sensor, $B_{3z}$ is a component of the magnetic induction intensity in the z direction measured by the fourth three-components magnetic measuring sensor.

Still another aspect of the present invention provides an apparatus for detecting the defect of the pipe including: a shelf provided above a pipe to be detected; a sliding track provided on the shelf and being able to slide along a length direction of the shelf; the device for detecting the defect of the pipe as described previously slidably connected to the sliding track through a slipper to detect the defect of the pipe of the pipe to be detected.

In the above-described apparatus for detecting the defect of the pipe, an actuating device for making the device for detecting the defect of the pipe to slide in uniform speed on the sliding track is provided.

In the above-described apparatus for detecting the defect of the pipe, the actuating device adopts any one of actuating manners including man-power, air pressure and hydraulic pressure.

With the method for detecting the defect of the pipe, the device for detecting the defect of the pipe and the apparatus for detecting the defect of the pipe of the present invention, whether there is the defect in the pipe can be decided based on parameters related to the magnetic induction intensity, and the position of the defect of the pipe can be determined according to a position at which the parameters are abnormal, and the degree of the defect of the pipe can be determined according to numerical values of the parameters which are abnormal. Accordingly, the position of the defect and the degree of the defect in the pipe can be detected accurately.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

According to a first embodiment of present invention, a method for detecting a defect of a pipe comprises the steps of: detecting a first parameter related to a magnetic induction intensity along a length direction of the pipe; determining whether the first parameter exceeds a predetermined threshold; determining a position at which the first parameter exceeds the predetermined threshold as a position of the defect of the pipe; and determining a degree of the defect of the pipe based on a numerical value of the first parameter exceeding the predetermined threshold.

With the method for detecting the defect of the pipe according to the first embodiment of the present invention, whether there is the defect in the pipe can be decided based on the first parameter related to the magnetic induction intensity, and further, the position of the defect of the pipe can be determined according to the position at which the parameter exceeds the predetermined threshold, and the degree of the defect of the pipe can be determined according to the numerical value of the first parameter exceeding the predetermined threshold. Thus, the method for detecting the defect of the pipe of the present invention can detect the defect in the pipe accurately, and determine the position of the defect and the degree of the defect accurately.

Figure 1:
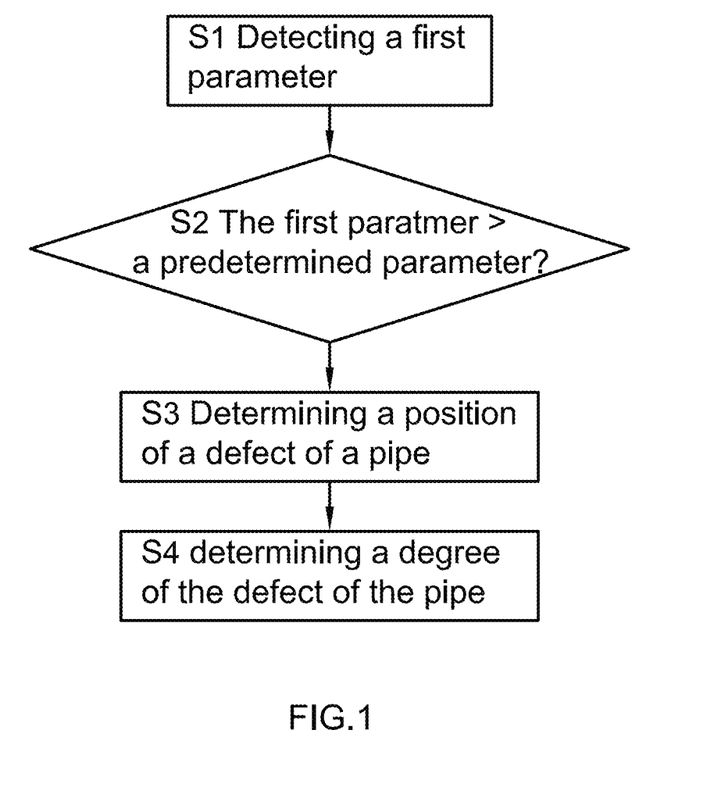
FIG. 1 is a schematic flow chart illustrating a method for detecting a defect of a pipe according to a first embodiment of present invention.

FIG. 1 is a schematic flow chart illustrating the method for detecting the defect of the pipe according to the first embodiment of present invention. As shown in FIG. 1, the method for detecting the defect of the pipe according to the first embodiment of the present invention comprises the step executed by a computer of: S1, detecting the first parameter related to the magnetic induction intensity along the length direction of the pipe; S2, determining whether the first parameter exceeds the predetermined threshold; S3, determining the position at which the first parameter exceeds the predetermined threshold as the position of the defect of the pipe; and S4, determining the degree of the defect of the pipe based on the numerical value of the first parameter exceeding the predetermined threshold.

Here, those skilled in the art can understand that, the first parameter can be detected continuously at respective points in the length direction of the pipe, or the first parameter can be detected discretely selectively at a plurality of points in the length direction of the pipe at the time of detecting the first parameter in the length direction of the pipe. That is, whether there is the defect at the detected position can be determined by detecting at a certain one or more points in the pipe.

In particular, the method for detecting the defect of the pipe according to the first embodiment of the present invention comprises the steps of: detecting the first parameter related to the magnetic induction intensity at a first point in the pipe; determining whether the first parameter exceeds the predetermined threshold; if the first parameter exceeds the predetermined threshold, determining the first point as the position of the defect in the pipe, and determining the degree of the defect at the first point based on the numerical value of the first parameter exceeding the predetermined threshold.

However, those skilled in the art can understand that, in order to ensure accuracy and fullness of the detection, the embodiments of the present invention preferably adopt a manner of a continuous detection. Also, those skilled in the art can understand that, the following description can be equally applied to a continuous detection and a discrete detection of the defect of the pipe, and the embodiments of the present invention do not intend to make any restriction thereto.

In the method for detecting the defect of the pipe according to the first embodiment of the present invention, the first parameter is a rate of change in a second direction of a component of the magnetic induction intensity in a first direction in a three-dimensional system of coordinate. Preferably, the first parameter is a rate of change in a second reference direction of a component of the magnetic induction intensity in a first reference direction in the three-dimensional system of coordinate. And, in the three-dimensional system of coordinate, the first direction may be same as the second direction, or may be different from the second direction.

Here, the reference direction in the three-dimensional system of coordinate refers to a x direction, a y direction or a z direction in the three-dimensional system of coordinate, and the first reference direction may be same as the second reference direction, or may be different from the second reference direction. For example, the first parameter is a rate of change in the y direction of a component $H_x$ of the magnetic induction intensity in the x direction in the three-dimensional system of coordinate, i.e., $\partial H_x/\partial y$, which is referred as $g_{xy}$ for brief. In this case, the first parameter is generally referred as a magnetic gradient, thus, $g_{xy}$ is also referred as a magnetic gradient in the y direction of the component of the magnetic induction intensity in the x direction. However, those skilled in the art can understand that, the first parameter may also be a rate of change in a certain direction or another direction of a component of the magnetic induction intensity in the certain direction in other coordinate systems. And, even in the three-dimensional system of coordinate having the x, the y and the z directions, the first reference direction and the second reference direction are not limited to the x, the y and the z directions, but may be for example a xy direction, a yz direction or the like. And, the first direction may be same as the second direction, or may be different from the second direction. For example, correspondingly, the first parameter may also be a rate of change in the x direction of a component $H_x$ of the magnetic induction intensity in the x direction in the three-dimensional system of coordinate, i.e., $\partial H_x/\partial x$, which is referred as $g_{xx}$ for brief. Therefore, regarding to the first parameter related to the magnetic induction intensity, so long as it can reflect the position of the defect and the degree of the defect of the pipe, the embodiments of the present invention do not intended to make any restriction.

Figure 2:
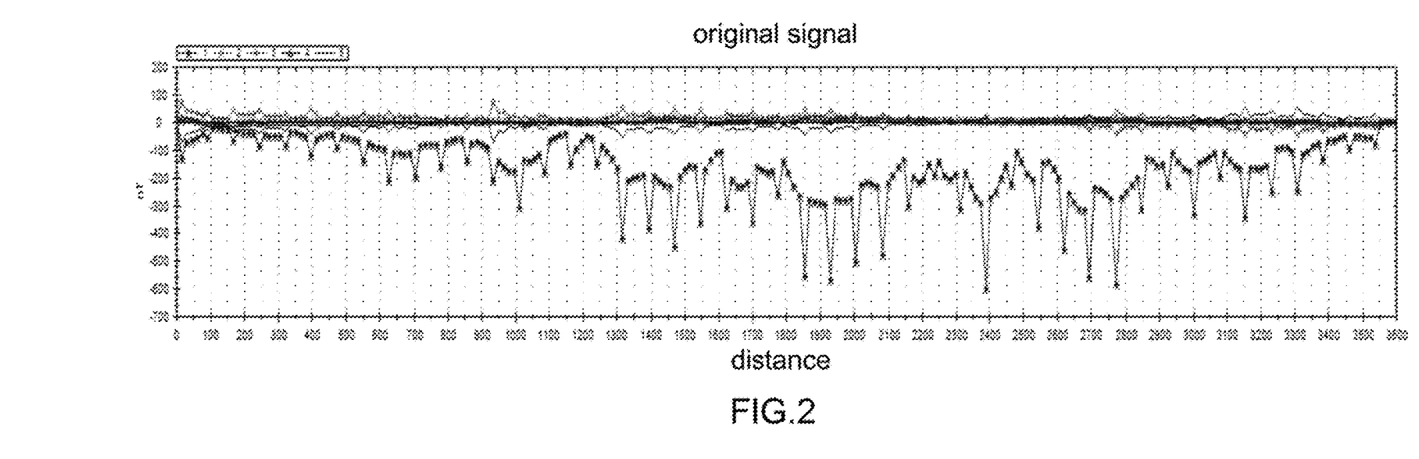
FIG. 2 is a schematic diagram of a graphical chart drawn by detecting 5 elements of a magnetic gradient matrix.

In the method for detecting the defect of the pipe according to the first embodiment of the present invention, after detecting the first parameter related to the magnetic induction intensity along the length direction of the pipe, a graphical chart of the magnitude of the first parameter versus a distance in the length direction of the pipe can be drawn. In particular, one end of the pipe detected is as an origin, a distance of the point detected from the origin is as a x coordinate, and the magnitude of the first parameter is as a y coordinate, a graphical chart in a x-y coordinate system is drawn, for example, as shown in FIG. 2. Thus, by viewing the graphical chart, the position of the defect and the degree of the defect of the pipe can be decided intuitively, so that displayed results are more intuitive.

In the method for detecting the defect of the pipe according to the first embodiment of the present invention, the step of determining the degree of the defect of the pipe based on the numerical value of the first parameter exceeding the predetermined threshold specifically comprises the steps of: determining the magnitude of the defect of the pipe based on an amplitude of the first parameter exceeding the predetermined threshold; and/or determining a length of the defect of the pipe based on a length in which the first parameter exceeds the predetermined threshold continuously.

As shown in FIG. 2, at the same time of determining that there is the defect in the pipe, a detailed instance of the defect of the pipe can be determined based on the numerical value of the first parameter. For example, the magnitude of the first parameter exceeding the predetermined threshold can reflect the magnitude of the defect of the pipe, that is, the larger the magnitude of the first parameter exceeding the predetermined threshold is, the larger the magnitude of the defect of the pipe is. Also, the length in which the first parameter exceeds the predetermined threshold continuously can reflect the length of the defect of the pipe, that is, the longer the length in which the first parameter exceeds the predetermined threshold continuously is, the longer the length of the defect of the pipe is. Also, based on specific characteristic of the first parameter and different data processing methods, other conditions of the defect of the pipe can be reflected, and the embodiments of the present invention do not list them one by one here.

In the method for detecting the defect of the pipe according to the first embodiment of the present invention, the method further comprises the steps of: detecting a second parameter related to the magnetic induction intensity along the length direction of the pipe; determining whether the second parameter exceeds the predetermined threshold; determining a position at which the second parameter exceeds the predetermined threshold as the position of the defect of the pipe; and determining the degree of the defect of the pipe based on the numerical value of the second parameter exceeding the predetermined threshold.

Here, in order to further improve accuracy of detection of the defect of the pipe, at the same time of detecting the first parameter related to the magnetic induction intensity along the length direction of the pipe, the method for detecting the defect of the pipe according to the first embodiment of the present invention further detects the second parameter related to the magnetic induction intensity along the length direction of the pipe. And preferably, the second parameter is a parameter associated with the first parameter, that is, the second parameter may be a rate of change in a fourth direction of a component of the magnetic induction intensity in a third direction in the three-dimensional system of coordinate. For example, the third direction and the fourth direction are also reference directions in the three-dimensional system of coordinate, and the second parameter is a rate of change in the z direction of a component $H_y$ of the magnetic induction intensity in the y direction in the three-dimensional system of coordinate, i.e., $\partial H_y/\partial z$, which is referred as $g_{yz}$ for brief. Similarly, the third direction may be same as the fourth direction, or may be different from the fourth direction. Thus, it would help to further determine the position of the defect and the degree of the defect in the pipe in assistance with the first parameter. Of course, those skilled in the art can understand that, the second parameter in the method for detecting the defect of the pipe according to the first embodiment of the present invention is not limited to the rate of change in the fourth direction of the component of the magnetic induction intensity in the third direction in the three-dimensional system of coordinate as the first parameter, as long as the second parameter can reflect the defect of the pipe detected. And, the second parameter does not have to be associated with the first parameter, and thus, the defect of the pipe can be detected in a plurality of perspectives, which avoid an instance in which a detection of a certain parameter is invalid due to some particular cases.

In a procedure of further determining the position of the defect and the degree of the defect in the pipe in assistance with the first parameter, when the position at which the first parameter exceeds the predetermined threshold is same as the position at which the second parameter exceeds the predetermined threshold, this position is determined as a position at which there is the defect in the pipe, and when the position at which the first parameter exceeds the predetermined threshold is different from the position at which the second parameter exceeds the predetermined threshold, both of the position at which the first parameter exceeds the predetermined threshold and the position at which the second parameter exceeds the predetermined threshold are determined as the position at which there is the defect in the pipe. And, when the position at which the first parameter exceeds the predetermined threshold is different from the position at which the second parameter exceeds the predetermined threshold, a detail of the defect of the pipe can be determined based on the numerical value of the first parameter and the numerical value of the second parameter respectively. Preferably, when the position at which the first parameter exceeds the predetermined threshold is same as the position at which the second parameter exceeds the predetermined threshold, the degree of the defect of the pipe is determined based on a larger one of the numerical value of the first parameter exceeding the predetermined threshold and the numerical value of the second parameter exceeding the predetermined threshold. In particular, the magnitude of the defect of the pipe is determined based on a larger one of the magnitude of the first parameter exceeding the predetermined threshold and the magnitude of the second parameter exceeding the predetermined threshold, and the length of the defect of the pipe is determined based on a larger one of the length in which the first parameter exceeds the predetermined threshold and the length in which the second parameter exceeds the predetermined threshold. Of course, according to specific characteristics of the first parameter and the second parameter, for example, a practical selection of the first parameter and the second parameter as well as association between the first parameter and the second parameter or the like, when the position at which the first parameter exceeds the predetermined threshold is same as the position at which the second parameter exceeds the predetermined threshold, the degree of the defect of the pipe at this position can be determined based on the numerical value of the first parameter and the numerical value of the second parameter in other manners, for example, in a manner of a weighted sum of the numerical value of the first parameter and the numerical value of the second parameter. Those skilled in the art can understand that, the embodiments of the present invention do not intend to make any form of restriction thereto.

Further, those skilled in the art can understand that, in addition to the first parameter and the second parameter, the method for detecting the defect of the pipe according to the first embodiment of the present invention can further detect other one or more parameters related to the magnetic induction intensity along the length direction of the pipe. For example, taking a rate of change in a certain reference direction of a component of the magnetic induction intensity in another reference direction in the three-dimensional system of coordinate as example, rates of change in the three directions of (x, y, z) in the coordinate system of three components of ($H_x$, $H_y$, $H_z$) of the magnetic induction intensity in three reference directions in the three-dimensional system of coordinate can be detected respectively. Thus, a magnetic gradient matrix including 9 elements in total can be constituted, the magnetic gradient matrix is referred as G, and is expressed as follows:

$$G = \begin{bmatrix} \partial H_x/\partial x & \partial H_x/\partial y & \partial H_x/\partial z \\ \partial H_y/\partial x & \partial H_y/\partial y & \partial H_y/\partial z \\ \partial H_z/\partial x & \partial H_z/\partial y & \partial H_z/\partial z \end{bmatrix} = \begin{bmatrix} a_{xx} & a_{xy} & a_{xz} \\ a_{yx} & a_{yy} & a_{yz} \\ a_{zx} & a_{zy} & a_{zz} \end{bmatrix} \quad \text{Formula 1}$$

And, in a passive space, a divergence degree and a rotation degree of the magnetic induction intensity are 0, that is, $$\begin{cases} \dfrac{\partial H_x}{\partial z} - \dfrac{\partial H_z}{\partial x} = 0 \\ \dfrac{\partial H_x}{\partial y} - \dfrac{\partial H_y}{\partial x} = 0 \\ \dfrac{\partial H_y}{\partial z} - \dfrac{\partial H_z}{\partial y} = 0 \end{cases} \quad \text{Formula 2}$$

Thus, in the 9 elements in the magnetic gradient matrix, only values of 5 mutually independent elements need to be obtained to calculate values of all elements in the matrix; of course, in practical applications, an operator can select to detect values of 6 elements, 7 elements, 8 elements or even all 9 elements, but actually, only 5 values need to be measured to calculate to obtain other values, so as to obtain the above-mentioned magnetic gradient matrix.

At the time of detecting one or more parameters related to the magnetic induction intensity, as explained in the above, a defect figure can be drawn so as to make status of the defect of the pipe more intuitive. FIG. 2 is a schematic diagram of a graphical chart drawn by detecting 5 elements of a magnetic gradient matrix. As shown in FIG. 2, by detecting values of 5 independent elements in the 9 elements in the above-described magnetic gradient matrix and drawing a curve of the values of the 5 elements versus a distance in the x–y coordinate system, 5 curves shown in this figure are obtained.

In the method for detecting the defect of the pipe according to the first embodiment of the present invention, the predetermined threshold can be selected by those skilled in the art in terms of experience, or may be set as a fixed value, for example, average value of the first parameter in a length of the entire pipe or the like, as long as whether there is the defect as well as the degree of the defect can be determined accurately by comparing the first parameter and the predetermined threshold.

Preferably, in the method for detecting the defect of the pipe according to the first embodiment of the present invention, in order to make the comparison between the first parameter and the predetermined threshold to reflect whether there is the defect accurately, and make the numerical value of the first parameter reflect the degree of the defect accurately, the first parameter is processed and the predetermined threshold is set as follows. In particular, determining whether the first parameter exceeds the predetermined threshold specifically includes: executing a differential processing on the first parameter; adding a variance of n times to/subtracting the variance of n times from an average value of the magnitude of the first parameter after differential processing as the predetermined threshold, wherein 1≤n≤3; and determining whether the first parameter exceeds the predetermined threshold.

Hereinafter, it is explained by taking executing the differential processing on the magnetic induction intensity as example, and at the time of executing the differential processing, the magnetic induction intensity of adjacent points are differentiated, as shown in the following formulae 3:

$$E'(x) = \lim_{\Delta x \to 0} \frac{\Delta E}{\Delta x} - \lim_{\Delta x \to 0} \frac{E(x + \Delta x) - E(x)}{\Delta x} \quad \text{Formula 3}$$

Wherein, E(x) expresses the magnetic induction intensity at a position of x, and E(x+Δx) expresses the magnetic induction intensity at a position of x+Δx. Thus, a result after the differential processing of E'(x) can be obtained, and it can express a magnitude of changes of the magnetic field at forward and backward position and can be used to determine whether there is the defect and the position at which the defect is.

Here, at the time of determining whether there is the defect, a variance of the change of the magnetic induction intensity is derived for the detected magnetic induction intensity according to a principle of mathematical statistics, as shown in the following Formulae 4:

$$D(E) = \frac{1}{n-1} \sum_{x=1}^{n} [E(x) - \overline{E}]^2 \quad \text{Formula 4}$$

wherein, $$\overline{E} = \frac{1}{n} \sum_{x=1}^{n} E(x).$$

And, according to the principle of mathematical statistics, the defect can be decided when E'(x)>|nD(x)|, and a magnitude of a value of n is determined according to the magnitude of the defect to be detected, and generally 1≤n≤3.

Of course, those skilled in the art can understand, hereinbefore, it is explained by taking the magnetic induction intensity as example. When the first parameter is other parameter related to the magnetic induction intensity, it may be executed the differential processing in a similar manner, and determine corresponding threshold. Therefore, in order not to confuse a substantial feature of this application, it no longer explained detailed here.

Figure 3:
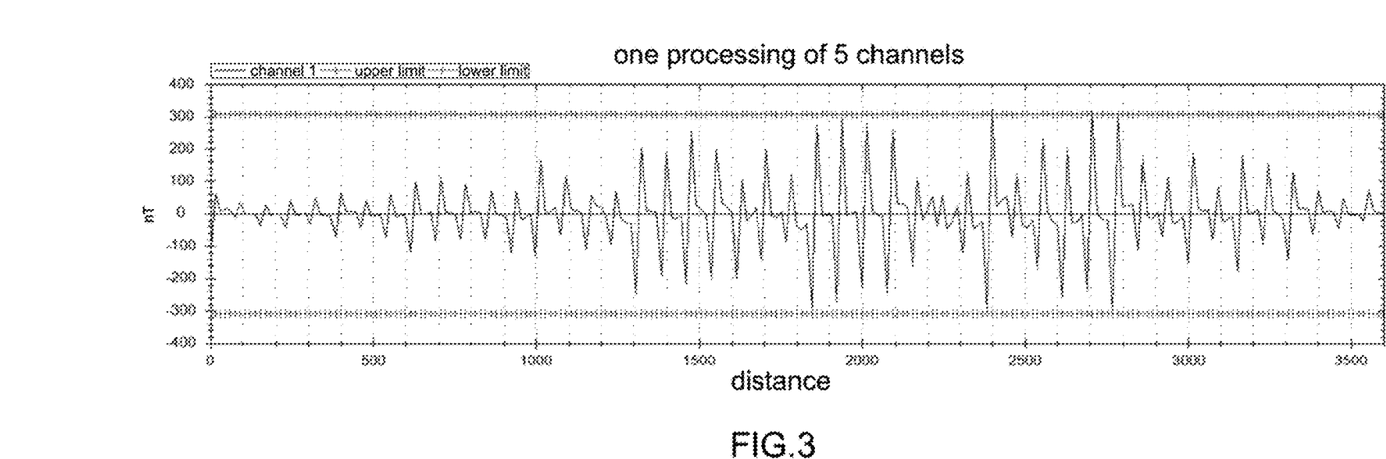
FIG. 3 is a schematic diagram of a curve obtained by executing a differential processing on one curve in FIG. 2.

FIG. 3 is a schematic diagram of a curve obtained by executing the differential processing on one curve in FIG. 2. As shown in FIG. 3, after executing the differential processing to one curve in FIG. 2, top-and-bottom defect threshold lines representing the predetermined threshold are further provided in the curve in FIG. 3. In FIG. 3, three times of variance is added to/subtracted from an average value of the magnitude of the first parameter after the differential processing, and the result is set as the top-and-bottom defect threshold lines. Thus, a case that the first parameter after the differential processing exceeds the predetermined threshold can be seen intuitively from FIG. 3.

Figure 4:
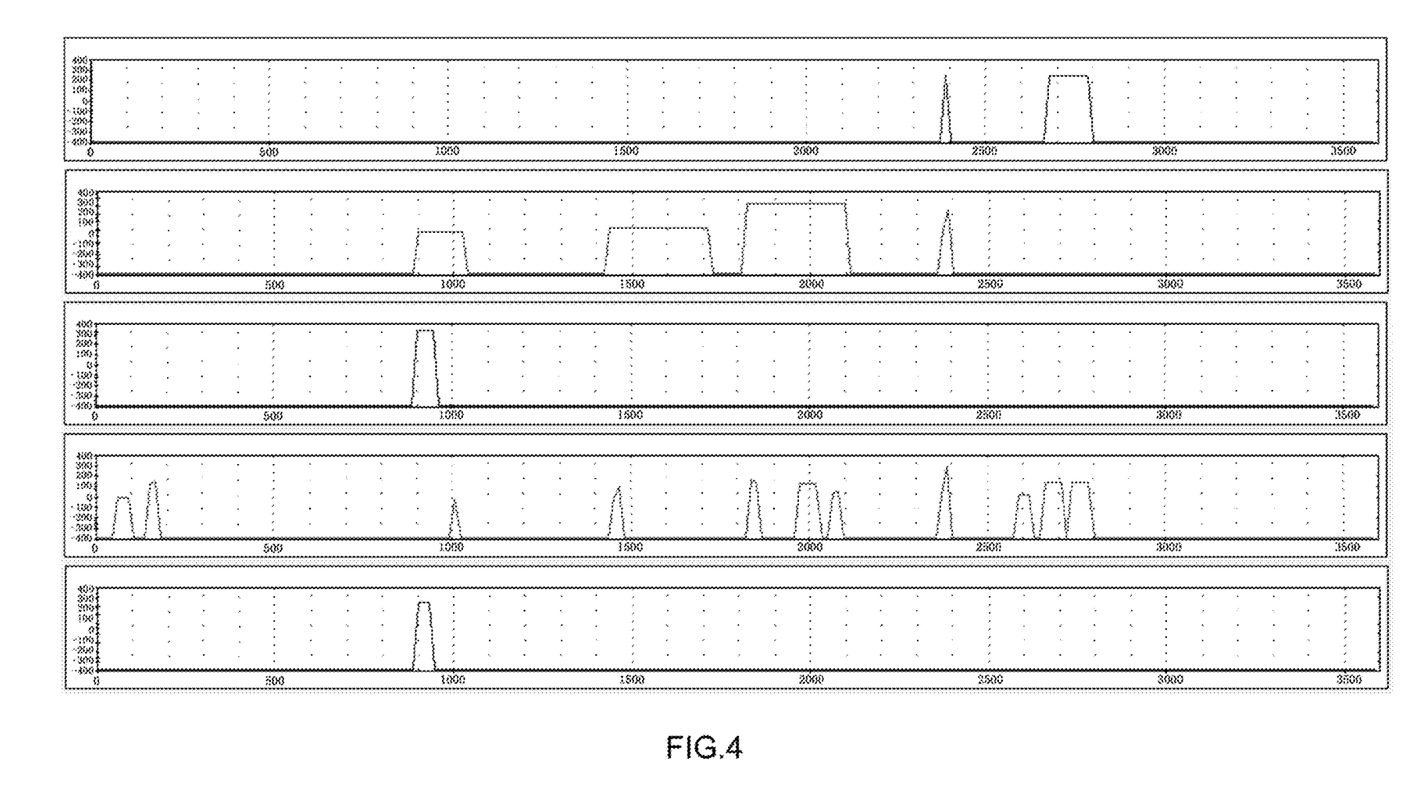
FIG. 4 is a schematic diagram of abnormal areas presented after processing of 5 curves shown in FIG. 2.

A part of the first parameter after the differential processing exceeding the predetermined threshold in FIG. 3 is intercepted, to represent an abnormal area in which the first parameter related to the magnetic induction intensity has abnormality in entire length of the pipe intuitively. FIG. 4 is a schematic diagram presenting the abnormal area after processing 5 curves shown in FIG. 2. As shown in FIG. 4, wherein 3 curves have abnormality after being processed, and 2 curves do not have abnormality after being processed.

Figure 5:
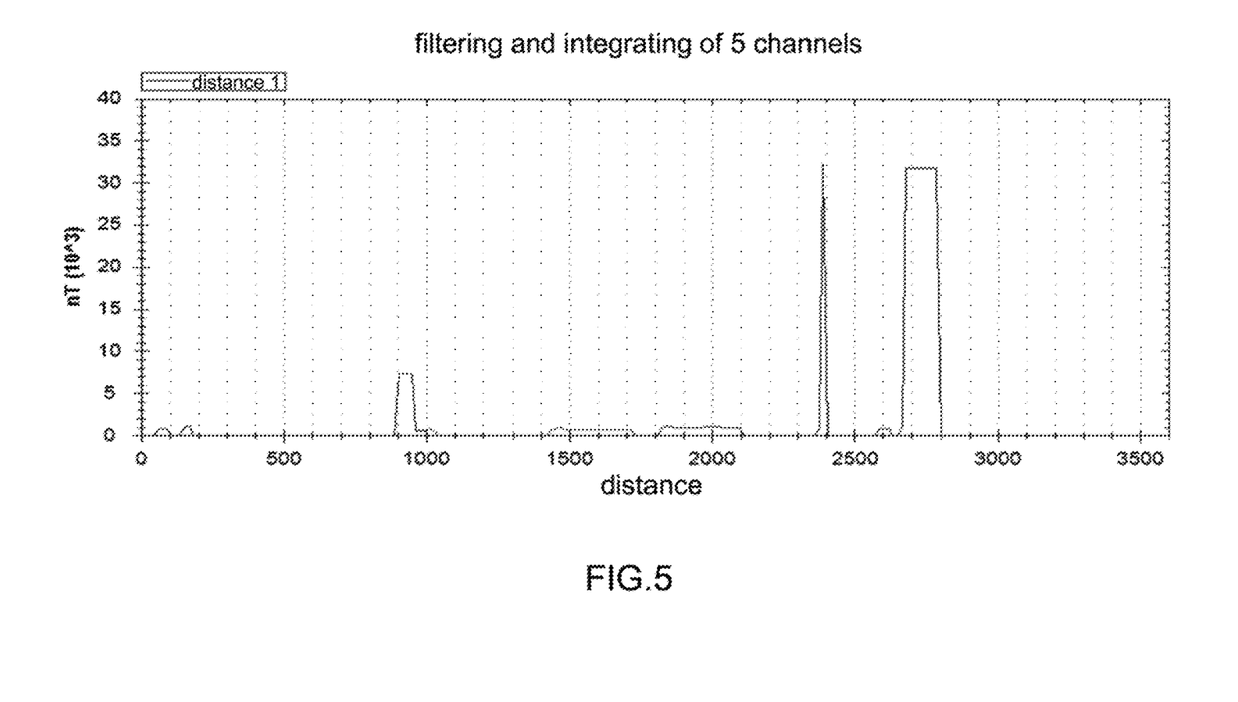
FIG. 5 is a schematic diagram after integrating the abnormal areas presented after processing as shown in FIG. 4.

Then, the abnormal areas presented by the plurality of curves are integrated according to the above method. That is, abnormal areas at same position in the x axis direction are merged and maximum value thereof is taken, and abnormal areas at different positions in the x axis direction are reserved. Thus, abnormal areas presented by the 5 curves as shown in FIG. 4 after being processed are integrated into a diagram, so as to present the position of the defect and the degree of the defect in the pipe clearly, as shown in FIG. 5. FIG. 5 is a schematic diagram after integrating the abnormal areas presented after the processing as shown in FIG. 4.

In the method for detecting the defect of the pipe according to the first embodiment of the present invention, the step of determining whether the first parameter exceeds the predetermined threshold further comprises the steps of: in case that there is no pipe to be detected, detecting a third parameter related to the magnetic induction intensity at respective points along the length direction of the pipe, wherein the third parameter is a parameter which is same as the first parameter; and in the case that the first parameter is larger than the third parameter, optimizing the first parameter with the third parameter, and determining whether the optimized first parameter exceeds the predetermined threshold.

In practice, even in case that there is no pipe to be detected, an ambient field having a certain magnetic induction intensity may be in a space to be detected, so as to make the first parameter related to the magnetic induction intensity not to reflect abnormality of the pipe accurately. Therefore, preferably, at the time of determining whether the first parameter exceeds the predetermined threshold, the first parameter is optimized by using data obtained by detecting the ambient field, so as to make the first parameter reflect the abnormality of the pipe more accurately. For example, in case that the first parameter is a rate of change in the y direction of a component $H_x$ of the magnetic induction intensity in the x direction in the three-dimensional system of coordinate, i.e., $g_{xy}$, a rate of change in the y direction of a component $H_x$ of the magnetic induction intensity in the x direction in the three-dimensional system of coordinate are measured at the respective points along the length direction of the pipe in a same manner in case that there is no pipe to be detected, and it is referred as $g'_{xy}$. Then, the value of $g_{xy} - g'_{xy}$ is as an optimized $g_{xy}$, and is determined whether it exceeds the predetermined threshold. Of course, those skilled in the art can understand that, the first parameter can be optimized with the third parameter in other manners, for example, it may decide that whether a magnitude of the first parameter is larger than a peak magnitude of the third parameter, so as to decide whether the detected first parameter is larger than data of the ambient field, and take the first parameter larger than the data of the ambient field as a reference of deciding whether it is the defect of the pipe. Further, a step of optimizing the first parameter with the data of the ambient field may be before the step of processing data of the first parameter and comparing with the predetermined threshold, or may be after the step of processing data of the first parameter and comparing with the predetermined threshold. If the first parameter is optimized with the data of the ambient field after processing the data of the first parameter and comparing with the predetermined threshold, the data of the ambient field should be processed correspond to the first parameter and compared with the predetermined threshold. For example, the third parameter of the ambient field is executed the differential processing, and top-and-bottom defect threshold lines are set. And in this case, abnormal areas caused by the ambient field can be taken out from the abnormal areas presented by the first parameter directly, or the abnormal areas presented by the first parameter is optimized with the abnormal areas caused by the ambient field.

Figure 6:
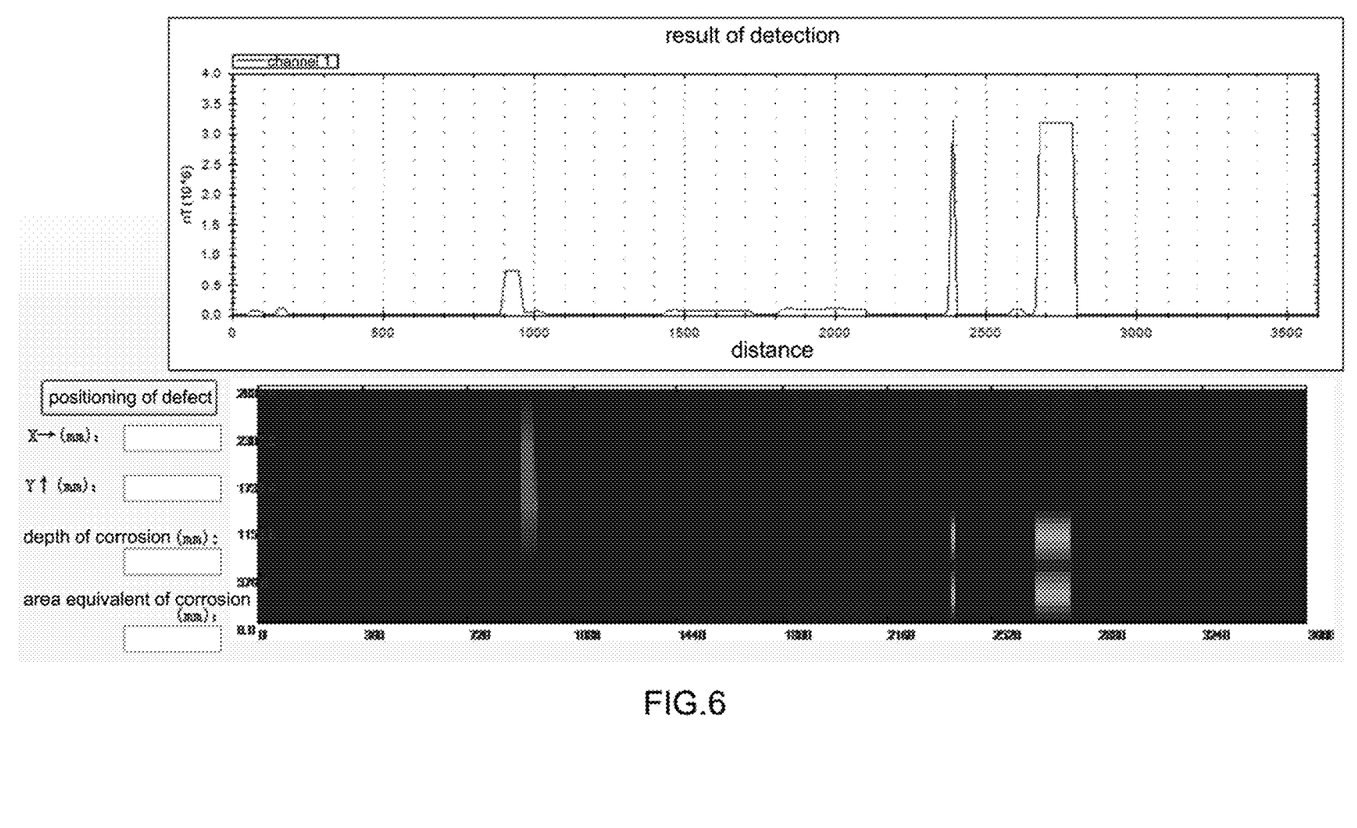
FIG. 6 is a schematic diagram of the defect of the pipe made based on the abnormal areas integrated as shown in FIG. 5.

In the method for detecting the defect of the pipe according to the first embodiment of the present invention, after optimizing the abnormal areas presenting magnetic abnormality according to the ambient field, the position of the defect, the length of the defect and the magnitude of the defect in the pipe can be decided specifically according to abnormal features in the respective magnetic abnormal area including start and end position of the magnetic abnormality and amplitude value of the magnetic abnormality, so as to obtain a final defect displaying result. A schematic diagram of the defect of the pipe can be further made by determining the position of the defect by a horizontal coordinate, determining the length of the defect by a length of the horizontal coordinate of the magnetic abnormal area and determining the magnitude of the defect by a vertical ordinate, for example, as shown in FIG. 6. FIG. 6 is a schematic diagram of the defect of the pipe made based on the abnormal areas integrated as shown in FIG. 5. Thus, the defect in the pipe can be known more intuitively as compared to the graphical diagram, so that it is easy for a maintainer of the pipe to take repair and maintenance work with respect to the defect of the pipe, which reduces cost and facilitates convenience.

Thus, with the method for detecting the defect of the pipe according to the first embodiment of the present invention, the position of the defect in the pipe can be detected accurately, and the degree of the defect can be determined accurately, so as to save cost of detection and repair of the pipe and facilitate convenience of the user.

A second embodiment of the present invention provides a device for detecting the defect of the pipe comprising the following modules being executed by a computer: a detecting unit configured to detect a first parameter related to a magnetic induction intensity along a length direction of the pipe; a deciding unit configured to determine whether the first parameter exceeds a predetermined threshold; and a control unit configured to determine a position at which the first parameter exceeds the predetermined threshold as the position of the defect of the pipe, and determining a degree of the defect of the pipe based on a numerical value of the first parameter exceeding the predetermined threshold.

Figure 7:
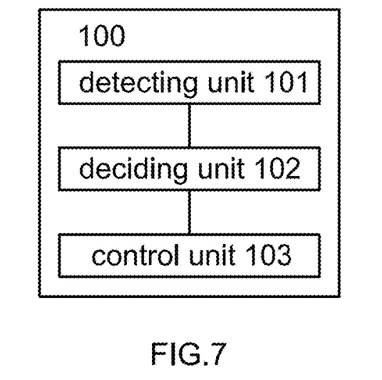
FIG. 7 is a schematic block diagram illustrating a device for detecting the defect of the pipe according to a second embodiment of the present invention.

FIG. 7 is a schematic block diagram illustrating a device for detecting the defect of the pipe according to a second embodiment of the present invention. As shown in FIG. 7, the device for detecting the defect of the pipe 100 according to the second embodiment of the present invention includes: a detecting unit 101 configured to detect the first parameter related to the magnetic induction intensity along the length direction of the pipe; a deciding unit 102 configured to determine whether the first parameter exceeds the predetermined threshold based on the first parameter detected by the detecting unit 101; and a control unit 103 configured to determine the position at which the first parameter exceeds the predetermined threshold as the position of the defect of the pipe based on a result of whether the first parameter exceeds the predetermined threshold determined by the deciding unit 102, and determine the degree of the defect of the pipe based on the numerical value of the first parameter exceeding the predetermined threshold.

In the above-described device for detecting the defect of the pipe, the first parameter is a rate of change in a second direction of a component of the magnetic induction intensity in a first direction in a three-dimensional system of coordinate.

In the above-described device for detecting the defect of the pipe, the first direction is same as the second direction, or the first direction is different from the second direction.

In the above-described device for detecting the defect of the pipe, the control unit further comprises: a magnitude of defect determining module configured to determine the magnitude of the defect of the pipe based on the magnitude of the first parameter exceeding the predetermined threshold: and/or a length of defect determining module configured to determine a length of the defect of the pipe based on a length in which the first parameter exceeds the predetermined threshold continuously.

In the above-described device for detecting the defect of the pipe, the device further comprises a drawing unit configured to draw a graphical chart of the magnitude of the first parameter versus a distance in the length direction of the pipe based on the first parameter detected by the detecting unit.

In the above-described device for detecting the defect of the pipe, the detecting unit is further configured to detect a second parameter related to the magnetic induction intensity along the length direction of the pipe; the deciding unit is further configured to determine whether the second parameter exceeds the predetermined threshold; and the control unit is further configured to determine a position at which the second parameter exceeds the predetermined threshold as the position of the defect of the pipe, and determine the degree of the defect of the pipe based on a numerical value of the second parameter exceeding the predetermined threshold.

In the above-described device for detecting the defect of the pipe, when the position at which the first parameter exceeds the predetermined threshold is same as the position at which the second parameter exceeds the predetermined threshold, the control unit determines the magnitude of the defect of the pipe based on the numerical value of the first parameter exceeding the predetermined threshold and the numerical value of the second parameter exceeding the predetermined threshold.

In the above-described device for detecting the defect of the pipe, the second parameter is a rate of change in a fourth direction of a component of the magnetic induction intensity in a third direction in the three-dimensional system of coordinate.

In the above-described device for detecting the defect of the pipe, the third direction is same as the fourth direction, or the third direction is different from the fourth direction.

In the above-described device for detecting the defect of the pipe, the first direction, the second direction, the third direction and the fourth direction are one of a x direction, a y direction and a z direction in the three-dimensional system of coordinate.

In the above-described device for detecting the defect of the pipe, the deciding unit further comprises: a differential processing module configured to execute a differential processing on the first parameter; a arithmetic processing module configured to add a variance of n times to/subtract the variance of n times from an average value of the first parameter after the differential processing of the differential processing module as the predetermined threshold, wherein $1 \leq n \leq 3$; and a deciding module configured to determine whether the first parameter exceeds the predetermined threshold.

In the above-described device for detecting the defect of the pipe, the detecting unit is further configured to detect a third parameter related to the magnetic induction intensity along the length direction of the pipe in case that there is no pipe to be detected, wherein the third parameter is a parameter which is same as the first parameter; and the deciding unit is further configured to optimize the first parameter with the third parameter in the case that the first parameter is larger than the third parameter, and determine whether the optimized first parameter exceeds the predetermined threshold.

In the above-described device for detecting the defect of the pipe, the detecting unit is further configured to, in addition to the first parameter and the second parameter related to the magnetic induction intensity, further detect rates of change in three directions x, y and z in the coordinate system of three components $H_x$, $H_y$ and $H_z$ of the magnetic induction intensity in three reference directions in the three-dimensional system of coordinate along the length direction of the pipe respectively, to constitute a magnetic gradient matrix G including 9 elements in total:

$$G = \begin{bmatrix} \partial H_x/\partial x & \partial H_x/\partial y & \partial H_x/\partial z \\ \partial H_y/\partial x & \partial H_y/\partial y & \partial H_y/\partial z \\ \partial H_z/\partial x & \partial H_z/\partial y & \partial H_z/\partial z \end{bmatrix} = \begin{bmatrix} a_{xx} & a_{xy} & a_{xz} \\ a_{yx} & a_{yy} & a_{yz} \\ a_{zx} & a_{zy} & a_{zz} \end{bmatrix}$$

In the above-described device for detecting the defect of the pipe, the detecting unit specifically comprises: a first three-components magnetic measuring sensor, a second three-components magnetic measuring sensor arranged symmetrically with a center of the detecting unit to the first three-components magnetic measuring sensor, a third three-components magnetic measuring sensor and a fourth three-components magnetic measuring sensor arranged symmetrically with a center of the detecting unit to the third three-components magnetic measuring sensor, wherein the first, the second, the third and the fourth three-components magnetic measuring sensors are cross-arranged in a plane; and each magnetic measuring sensor in the first, the second, the third and the fourth three-components magnetic measuring sensors calculate a magnetic gradient of a central position of the cross by detecting values of magnetic induction intensity in three reference directions in the three-dimensional system of coordinate thereof, so as to measure the magnetic gradient matrix G at the central position of the cross:

$$G = \begin{bmatrix} \partial H_x/\partial x & \partial H_x/\partial y & \partial H_x/\partial z \\ \partial H_y/\partial x & \partial H_y/\partial y & \partial H_y/\partial z \\ \partial H_z/\partial x & \partial H_z/\partial y & \partial H_z/\partial z \end{bmatrix} = \begin{bmatrix} a_{xx} & a_{xy} & a_{xz} \\ a_{yx} & a_{yy} & a_{yz} \\ a_{zx} & a_{zy} & a_{zz} \end{bmatrix} =$$

$$\begin{bmatrix} \dfrac{B_{1x}-B_{3x}}{\Delta x} & \dfrac{B_{1y}-B_{3y}}{\Delta x} & \dfrac{B_{2x}-B_{0x}}{\Delta z} \\ \dfrac{B_{1y}-B_{3y}}{\Delta x} & -\left(\dfrac{B_{1x}-B_{3x}}{\Delta x}+\dfrac{B_{2z}-B_{0z}}{\Delta z}\right) & \dfrac{B_{2y}-B_{0y}}{\Delta z} \\ \dfrac{B_{1z}-B_{3z}}{\Delta x} & \dfrac{B_{2y}-B_{0y}}{\Delta z} & \dfrac{B_{2z}-B_{0z}}{\Delta z} \end{bmatrix}$$

wherein, $\Delta x$ is a distance between the first three-components magnetic measuring sensor and the second three-components magnetic measuring sensor, $\Delta z$ is a distance between the third three-components magnetic measuring sensor and the fourth three-components magnetic measuring sensor, $B_{1x}$ is a component of the magnetic induction intensity in the x direction measured by the first three-components magnetic measuring sensor, $B_{1y}$ is a component of the magnetic induction intensity in the y direction measured by the first three-components magnetic measuring sensor, $B_{1z}$ is a component of the magnetic induction intensity in the z direction measured by the first three-components magnetic measuring sensor; $B_{2x}$ is a component of the magnetic induction intensity in the x direction measured by the second three-components magnetic measuring sensor, $B_{2y}$ is a component of the magnetic induction intensity in the y direction measured by the second three-components magnetic measuring sensor, $B_{2z}$ is a component of the magnetic induction intensity in the z direction measured by the second three-components magnetic measuring sensor; $B_{0x}$ is a component of the magnetic induction intensity in the x direction measured by the third three-components magnetic measuring sensor, $B_{0y}$ is a component of the magnetic induction intensity in the y direction measured by the third three-components magnetic measuring sensor, $B_{0z}$ is a component of the magnetic induction intensity in the z direction measured by the third three-components magnetic measuring sensor; $B_{3x}$ is a component of the magnetic induction intensity in the x direction measured by the fourth three-components magnetic measuring sensor, $B_{3y}$ a component of the magnetic induction intensity in the y direction measured by the fourth three-components magnetic measuring sensor, $B_{3z}$ is a component of the magnetic induction intensity in the z direction measured by the fourth three-components magnetic measuring sensor.

Figure 8:
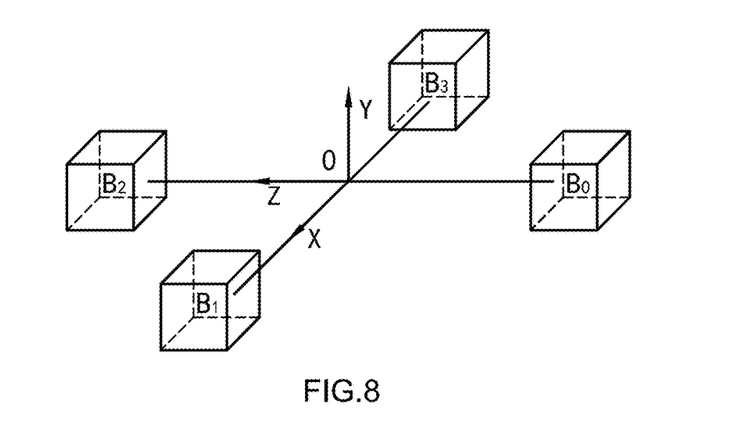
FIG. 8 is a schematic diagram of a magnetic gradient detecting component according to the embodiments of the present invention.

As explained above, in the method for detecting the defect of the pipe according to the first embodiment of the present invention and the device for detecting the defect of the pipe according to the second embodiment of the present invention, a rate of change in a certain reference direction of a component of the magnetic induction intensity in another reference direction in the three-dimensional system of coordinate can be taken as the first parameter related to the magnetic induction intensity, and in this case the first parameter is referred as the magnetic gradient generally, and the parameter is detected by using a corresponding magnetic gradient detection device. FIG. 8 is a schematic diagram of a magnetic gradient detecting component according to the embodiments of the present invention. As shown in FIG. 8, a magnetic gradient detecting component 200 according to the embodiments of the present invention includes 4 three-components magnetic measuring sensors $B_0$, $B_1$, $B_2$ and $B_3$ cross-arranged in a plane, a magnetic gradient of a central position of the cross is calculated by detecting values of magnetic induction intensities in three directions of each magnetic measuring sensor in the 4 three-components magnetic measuring sensors, so as to measure a magnetic gradient matrix in the central position of the cross. Of course, those skilled in the art can understand that, the value of the magnetic gradient measured by the magnetic gradient detecting component 200 as shown in FIG. 8 would be more accurate, however, in the method for detecting the defect of the pipe and the device for detecting the defect of the pipe according to the embodiments of the present invention, other types of magnetic gradient detecting component can be used to detect.

As shown in FIG. 8, the magnetic gradient measuring device 100 adopting the 4 magnetic measuring sensors $B_0$, $B_1$, $B_2$ and $B_3$ cross-arranged can detect the magnetic gradient, wherein each of the 4 magnetic measuring sensors $B_0$, $B_1$, $B_2$ and $B_3$ is the three-components magnetic measuring sensor, that is, it can measure a component of the magnetic induction intensity in the x, the y and the z direction. As shown in FIG. 8, in one plane, $B_0$ and $B_2$ are provided symmetrically, $B_1$ and $B_3$ are provided symmetrically, and a distance from the $B_0$ to the center, a distance from the $B_2$ to the center, a distance from the $B_1$ to the center and a distance from the $B_3$ to the center are all identical. Of course, those skilled in the art can understand that, in practical applications, as long as $B_0$ and $B_2$ are provided symmetrically and $B_1$ and $B_3$ are provided symmetrically, a distance between the $B_0$ and the $B_2$ may be different from a distance between the $B_1$ and $B_3$, setting these distances to be identical is only for convenience of calculation of the magnetic gradient. Then, a magnetic gradient matrix at a central point obtained by the magnetic gradient measuring device 100 is:

$$G = \begin{bmatrix} \partial H_x/\partial x & \partial H_x/\partial y & \partial H_x/\partial z \\ \partial H_y/\partial x & \partial H_y/\partial y & \partial H_y/\partial z \\ \partial H_z/\partial x & \partial H_z/\partial y & \partial H_z/\partial z \end{bmatrix} = \begin{bmatrix} a_{xx} & a_{xy} & a_{xz} \\ a_{yx} & a_{yy} & a_{yz} \\ a_{zx} & a_{zy} & a_{zz} \end{bmatrix} =$$

$$\begin{bmatrix} \dfrac{B_{1x}-B_{3x}}{\Delta x} & \dfrac{B_{1y}-B_{3y}}{\Delta x} & \dfrac{B_{2x}-B_{0x}}{\Delta z} \\ \dfrac{B_{1y}-B_{3y}}{\Delta x} & -\left(\dfrac{B_{1x}-B_{3x}}{\Delta x}+\dfrac{B_{2z}-B_{0z}}{\Delta z}\right) & \dfrac{B_{2y}-B_{0y}}{\Delta z} \\ \dfrac{B_{1z}-B_{3z}}{\Delta x} & \dfrac{B_{2y}-B_{0y}}{\Delta z} & \dfrac{B_{2z}-B_{0z}}{\Delta z} \end{bmatrix}$$

In the above formula, $\Delta x$ is a distance between the $B_1$ sensor and the $B_3$ sensor, $\Delta z$ is a distance between the $B_0$ sensor and the $B_2$ sensor, $B_{1x}$ is a component of the magnetic induction intensity in the x direction measured by the $B_1$ sensor, $B_{1y}$ is a component of the magnetic induction intensity in the y direction measured by the $B_1$ sensor, $B_{1z}$ is a component of the magnetic induction intensity in the z direction measured by the $B_1$ sensor; $B_{2x}$ is a component of the magnetic induction intensity in the x direction measured by the $B_2$ sensor, $B_{2y}$ is a component of the magnetic induction intensity in the y direction measured by the $B_2$ sensor, $B_{2z}$ is a component of the magnetic induction intensity in the z direction measured by the $B_2$ sensor; $B_{0x}$ is a component of the magnetic induction intensity in the x direction measured by the $B_0$ sensor, $B_{0y}$ is a component of the magnetic induction intensity in the y direction measured by the $B_0$ sensor, $B_{0z}$ is a component of the magnetic induction intensity in the z direction measured by the $B_0$ sensor; $B_{3x}$ is a component of the magnetic induction intensity in the x direction measured by the $B_3$ sensor, $B_{3y}$ a component of the magnetic induction intensity in the y direction measured by the $B_3$ sensor, $B_{3z}$ is a component of the magnetic induction intensity in the z direction measured by the $B_3$ sensor. Values of 9 elements in the magnetic gradient matrix G can be obtained by measurement, however, similar to the above-mentioned, in practical application, since Formula 2 is satisfied, only values of 5 elements need to be obtained to derive the values of all 9 elements. And, from the above Formula, value of any one of component $H_x$, $H_y$ or $H_z$ of the magnetic induction intensity in the three reference directions in the three-dimensional system of coordinate can be obtained from the above formula, for example, $g_{xy}=(B_{1x}-B_{3x})/\Delta x$. Thus, value of required elements can be calculated as necessary.

And, those skilled in the art can understand that, when the first parameter related to the magnetic induction intensity is not the magnetic gradient, for example, it is an attenuation decrement of the magnetic induction intensity, it is detected by using different device, and the embodiments of the present invention do not intend to make any restriction thereto.

A third embodiment of the present invention provides an apparatus for detecting the defect of the pipe including: a shelf provided above a pipe to be detected; a sliding track provided on the shelf and being able to slide along a length direction of the shelf; the device for detecting the defect of the pipe as described previously slidably connected to the sliding track through a slipper to detect the defect of the pipe of the pipe to be detected.

In the above-described apparatus for detecting the defect of the pipe, an actuating device for making the device for detecting the defect of the pipe to slide in uniform speed on the sliding track is provided.

In the above-described apparatus for detecting the defect of the pipe, the actuating device adopts any one of actuating manners including man-power, air pressure and hydraulic pressure.

Figure 9:
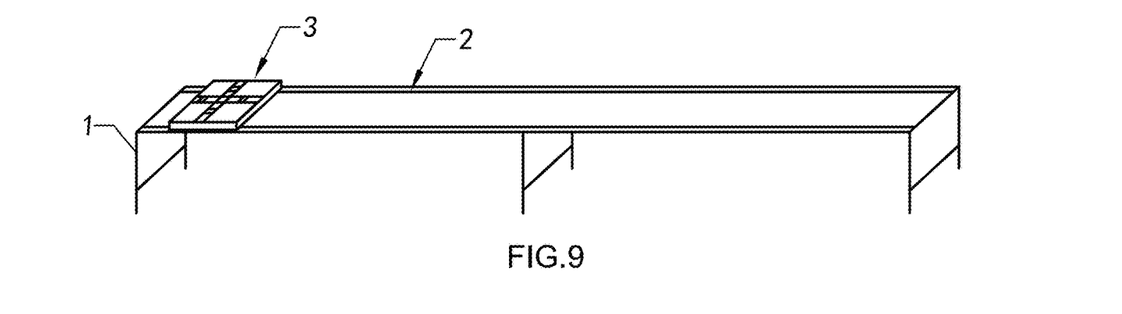
FIG. 9 is a schematic diagram illustrating an apparatus for detecting the defect of the pipe according to a third embodiment of the present invention.

FIG. 9 is a schematic diagram illustrating an apparatus for detecting the defect of the pipe according to a third embodiment of the present invention. As shown in FIG. 9, an apparatus for detecting the defect of the pipe 10 includes a shelf 1, a sliding track 2 and a device for detecting the defect of the pipe 3. The device for detecting the defect of the pipe 3 is disposed above a pipe by providing the shelf 1 on which the sliding track 2 is provided. The device for detecting the defect of the pipe 3 is slidably connected to the sliding track 2 through a slipper. At the time of detection, the shelf 1 is stationary, and the device for detecting the defect of the pipe 3 slides in uniform speed on the sliding track 2 to detect the pipe. The device for detecting the defect of the pipe 3 can slide in uniform speed on the sliding track 2 by an actuating device, and the actuating device can adopt man-power, air pressure, hydraulic pressure or the like to control a manner of an object moving in uniform speed on a rack arbitrarily. In case that a length of the shelf is less than a length of a pipe to be detected, after a detection at a position at which the shelf 1 is completed, the shelf 1 is moved in position to start a next detection. In this way, the device for detecting the defect of the pipe can eliminate problems of shake of moving the track or inconsistent speed of moving caused by controlling movement manually as large as possible, so that an external interference is least and a result of detection is more accurate.

With the method for detecting the defect of the pipe, the device for detecting the defect of the pipe and the apparatus for detecting the defect of the pipe of the present invention, whether there is the defect in the pipe can be decided based on parameters related to the magnetic induction intensity, and the position of the defect of the pipe can be determined according to a position at which the parameters are abnormal, and the degree of the defect of the pipe can be determined according to numerical values of the parameters which are abnormal. Accordingly, the position of the defect and the degree of the defect in the pipe can be detected accurately.

Of course, the present invention also has many other embodiments, and those skilled in the art can make various kinds of corresponding changes and variations according to the present invention without departing from a spirit and an essence of the present invention, however, these corresponding changes and variations all fall into a scope sought for protection of attached claims of the present invention.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method for detecting a defect of a pipe, comprising the steps of:
   (a) detecting a magnetic induction intensity along a length direction of the pipe by a magnetic measuring sensor, and determining a first parameter and a second parameter related to the magnetic induction intensity via a detecting unit, wherein the magnetic measuring sensor includes: a first three-components magnetic measuring sensor, a second three-components magnetic measuring sensor arranged symmetrically with a center of the detecting unit to the first three-components magnetic measuring sensor, a third three-components magnetic measuring sensor and a fourth three-components magnetic measuring sensor arranged symmetrically with a center of the detecting unit to the third three-components magnetic measuring sensor, wherein the first, the second, the third and the fourth three-components magnetic measuring sensors are cross-arranged in a plane; and each magnetic measuring sensor in the first, the second, the third and the fourth three-components magnetic measuring sensors calculate a magnetic gradient of a central position of the cross by detecting values of magnetic induction intensity in three reference directions in the three-dimensional system of coordinate thereof;
   (b) via said detecting unit, determining whether the first parameter exceeds a predetermined threshold and determining whether the second parameter exceeds the predetermined threshold;
   (c) via a control unit, determining a position at which the first parameter exceeds the predetermined threshold as the position of the defect of the pipe, and determining a position at which the second parameter exceeds the predetermined threshold as the position of the defect of the pipe;
   (d) via said control unit, determining a degree of the defect of the pipe based on a numerical value of the first parameter exceeding the predetermined threshold, and determining the degree of the defect of the pipe based on the numerical value of the second parameter exceeding the predetermined threshold; and
   (e) via said control unit, determining the position of the defect of the pipe when the position from the first parameter is the same as the position from the second parameter
   wherein the first parameter is a rate of change in a second direction of a component of the magnetic induction intensity in a first direction in a three-dimensional system of coordinate, wherein the second parameter is a rate of change in a fourth direction of a component of the magnetic induction intensity in a third direction in the three-dimensional system of coordinate, wherein the first parameter and the second parameter are selected from two parameters selected from the group consisting of $\partial Hx/\partial x$; $\partial Hx/\partial y$; $\partial Hx/\partial z$; $\partial Hy/\partial x$; $\partial Hy/\partial y$; $\partial Hy/\partial z$; $\partial Hz/\partial x$; $\partial Hz/\partial y$; and $\partial Hz/\partial z$.

2. The method, as recited in claim 1, wherein the first direction is different from the second direction, and the third direction is different from the fourth direction.

3. A device for detecting a defect of a pipe, comprising:
   a magnetic measuring sensor that detects a magnetic induction intensity along a length direction of the pipe, wherein the magnetic measuring sensor includes: a first three-components magnetic measuring sensor, a second three-components magnetic measuring sensor arranged symmetrically with a center thereof to the first three-components magnetic measuring sensor, a third three-components magnetic measuring sensor and a fourth three-components magnetic measuring sensor arranged symmetrically with a center thereof to the third three-components magnetic measuring sensor, wherein the first, the second, the third and the fourth three-components magnetic measuring sensors are cross-arranged in a plane; and each magnetic measuring sensor in the first, the second, the third and the fourth three-components magnetic measuring sensors calculate a magnetic gradient of a central position of the cross by detecting values of magnetic induction intensity in three reference directions in the three-dimensional system of coordinate thereof; and
   a computer executing the following modules:
   a detecting unit that determines a first parameter and a second parameter related to the magnetic induction intensity;
   a deciding unit configured to determine whether the first parameter exceeds a predetermined threshold and to determine whether the second parameter exceeds the predetermined threshold; and
   a control unit configured to determine a position at which the first parameter exceeds the predetermined threshold as a position of the defect of the pipe, and to determine a degree of the defect of the pipe based on a numerical value of the first parameter exceeding the predetermined threshold, wherein the control unit further determines a position at which the second parameter exceeds the predetermined threshold as a position of the defect of the pipe, and to determine a degree of the defect of the pipe based on a numerical value of the second parameter exceeding the predetermined threshold, wherein the position of the defect of the pipe is determined when the position from the first parameter is the same as the position from the second parameter, wherein the first parameter is a rate of change in a second direction of a component of the magnetic induction intensity in a first direction in a three-dimensional system of coordinate, wherein the second parameter is a rate of change in a fourth direction of a component of the magnetic induction intensity in a third direction in the three-dimensional system of coordinate, wherein the first parameter and the second parameter are selected from two parameters selected from the group consisting of $\partial Hx/\partial x$; $\partial Hx/\partial y$; $\partial Hx/\partial z$; $\partial Hy/\partial x$; $\partial Hy/\partial y$; $\partial Hy/\partial z$; $\partial Hz/\partial x$; $\partial Hz/\partial y$; and $\partial Hz/\partial z$.

4. The device, as recited in claim 3, wherein the control unit further comprises:
   a magnitude of defect determining module configured to determine the magnitude of the defect of the pipe based on a magnitude of the first parameter exceeding the predetermined threshold: and
a length of defect determining module configured to determine a length of the defect of the pipe based on a length in which the first parameter exceeds the predetermined threshold continuously.

5. The device, as recited in claim 3, further comprising a drawing unit configured to draw a graphical chart of the magnitude of the first parameter versus a distance in the length direction of the pipe based on the first parameter detected by the detecting unit.

6. The device, as recited in claim 3 further comprising a drawing unit configured to draw a graphical chart of the magnitude of the first parameter versus a distance in the length direction of the pipe based on the first parameter detected by the detecting unit.

7. The device, as recited in claim 3, wherein when the position at which the first parameter exceeds the predetermined threshold is same as the position at which the second parameter exceeds the predetermined threshold, the control unit determines the magnitude of the defect of the pipe based on the numerical value of the first parameter exceeding the predetermined threshold and the numerical value of the second parameter exceeding the predetermined threshold.

8. The device, as recited in claim 7, wherein the second parameter is a rate of change in a fourth direction of a component of the magnetic induction intensity in a third direction in the three-dimensional system of coordinate.

9. The device, as recited in claim 3, wherein the deciding unit further comprises:
a differential processing module configured to execute a differential processing on the first parameter;
an arithmetic processing module configured to add a variance of n times to/subtract the variance of n times from an average value of the first parameter after the differential processing of the differential processing module as the predetermined threshold, wherein $1 \leq n \leq 3$; and
a deciding module configured to determine whether the first parameter exceeds the predetermined threshold.

10. The device, as recited in claim 3, wherein the detecting unit is further configured to detect a third parameter related to the magnetic induction intensity along the length direction of the pipe in an ambient field, wherein the third parameter is a parameter which is same as the first parameter, wherein the deciding unit is further configured to optimize the first parameter with the third parameter in case that the first parameter is larger than the third parameter, and determine whether the optimized first parameter exceeds the predetermined threshold.

11. The device for detecting the defect of the pipe according to claim 8, wherein the detecting unit is further configured to, in addition to the first parameter and the second parameter related to the magnetic induction intensity, further detect rates of change in three directions X, Y and Z in the coordinate system of three components $H_x$, $H_y$ and $H_z$ of the magnetic induction intensity in three reference directions in the three-dimensional system of coordinate along the length direction of the pipe respectively, to constitute a magnetic gradient matrix G including 9 elements in total:

$$G = \begin{bmatrix} \partial H_x/\partial x & \partial H_x/\partial y & \partial H_x/\partial z \\ \partial H_y/\partial x & \partial H_y/\partial y & \partial H_y/\partial z \\ \partial H_z/\partial x & \partial H_z/\partial y & \partial H_z/\partial z \end{bmatrix} = \begin{bmatrix} a_{xx} & a_{xv} & a_{xz} \\ a_{vx} & a_{vv} & a_{vz} \\ a_{zx} & a_{zv} & a_{zz} \end{bmatrix}.$$

12. The device, as recited in claim 11, wherein the device is arranged to measure the magnetic gradient matrix G at the central position of the cross:

$$G = \begin{bmatrix} \partial H_x/\partial x & \partial H_x/\partial y & \partial H_x/\partial z \\ \partial H_y/\partial x & \partial H_y/\partial y & \partial H_y/\partial z \\ \partial H_z/\partial x & \partial H_z/\partial y & \partial H_z/\partial z \end{bmatrix} = \begin{bmatrix} a_{xx} & a_{xv} & a_{xz} \\ a_{vx} & a_{vv} & a_{vz} \\ a_{zx} & a_{zv} & a_{zz} \end{bmatrix} =$$

$$\begin{bmatrix} \dfrac{B_{1x}-B_{3x}}{\Delta x} & \dfrac{B_{1y}-B_{3y}}{\Delta x} & \dfrac{B_{2x}-B_{0x}}{\Delta z} \\ \dfrac{B_{1y}-B_{3y}}{\Delta x} & -\left(\dfrac{B_{1x}-B_{3x}}{\Delta x}+\dfrac{B_{2z}-B_{0z}}{\Delta z}\right) & \dfrac{B_{2y}-B_{0y}}{\Delta z} \\ \dfrac{B_{1z}-B_{3z}}{\Delta x} & \dfrac{B_{2y}-B_{0y}}{\Delta z} & \dfrac{B_{2z}-B_{0z}}{\Delta z} \end{bmatrix}$$

wherein, $\Delta x$ is a distance between the first three-components magnetic measuring sensor and the second three-components magnetic measuring sensor, $\Delta z$ is a distance between the third three-components magnetic measuring sensor and the fourth three-components magnetic measuring sensor, $B_{1x}$ is a component of the magnetic induction intensity in the X direction measured by the first three-components magnetic measuring sensor, $B_{1y}$ is a component of the magnetic induction intensity in they Y direction measured by the first three-components magnetic measuring sensor, $B_{1z}$ is a component of the magnetic induction intensity in the Z direction measured by the first three-components magnetic measuring sensor; $B_{2x}$ is a component of the magnetic induction intensity in the X direction measured by the second three-components magnetic measuring sensor, $B_{2y}$ is a component of the magnetic induction intensity in the Y direction measured by the second three-components magnetic measuring sensor, $B_{2z}$ is a component of the magnetic induction intensity in the Z direction measured by the second three-components magnetic measuring sensor; $B_{0x}$ is a component of the magnetic induction intensity in the X direction measured by the third three-components magnetic measuring sensor, $B_{0y}$ is a component of the magnetic induction intensity in the Y direction measured by the third three-components magnetic measuring sensor, $B_{0z}$ is a component of the magnetic induction intensity in the Z direction measured by the third three-components magnetic measuring sensor; $B_{3x}$ is a component of the magnetic induction intensity in the X direction measured by the fourth three-components magnetic measuring sensor, $B_{3y}$ a component of the magnetic induction intensity in the Y direction measured by the fourth three-components magnetic measuring sensor, $B_{3z}$ is a component of the magnetic induction intensity in the Z direction measured by the fourth three-components magnetic measuring sensor.

13. An apparatus for detecting a defect of a pipe, comprising:
a shelf provided above a pipe, wherein the pipe is to be detected;
a sliding track provided on the shelf along a length direction of the shelf; and
a device slidably connected to the sliding track through a slipper for detecting the defect of the pipe, wherein the device comprises:
a magnetic measuring sensor that detects a magnetic induction intensity along a length direction of the pipe, wherein the magnetic measuring sensor includes: a first three-components magnetic measuring sensor, a second three-components magnetic measuring sensor arranged symmetrically with a center thereof to the first three-components magnetic measuring sensor, a third three-components magnetic measuring sensor and a fourth three-components magnetic measuring sensor arranged symmetrically with a center thereof to the third three-components magnetic measuring sensor, wherein the first, the second, the third and the fourth three-components magnetic measuring sensors are cross-arranged in a plane; and each magnetic measuring sensor in the first, the second, the third and the fourth three-components magnetic measuring sensors calculate a magnetic gradient of a central position of the cross by detecting values of magnetic induction intensity in three reference directions in the three-dimensional system of coordinate thereof; and a computer executing the following modules:

a detecting unit that determines a first parameter and a second parameter related to the magnetic induction intensity;

a deciding unit configured to determine whether the first parameter exceeds a predetermined threshold and to determine whether the second parameter exceeds the predetermined threshold; and a control unit configured to determine a position at which the first parameter exceeds the predetermined threshold as a position of the defect of the pipe, and to determine a degree of the defect of the pipe based on a numerical value of the first parameter exceeding the predetermined threshold, wherein the control unit further determines a position at which the second parameter exceeds the predetermined threshold as a position of the defect of the pipe, and to determine a degree of the defect of the pipe based on a numerical value of the second parameter exceeding the predetermined threshold, wherein the defect of the pipe is determined when the position from the first parameter is the same as the position from the second parameter, wherein the first parameter is a rate of change in a second direction of a component of the magnetic induction intensity in a first direction in a three-dimensional system of coordinate, wherein the second parameter is a rate of change in a fourth direction of a component of the magnetic induction intensity in a third direction in the three-dimensional system of coordinate, wherein the first parameter and the second parameter are selected from two parameters selected from the group consisting of $\partial Hx/\partial x$; $\partial Hx/\partial y$; $\partial Hx/\partial z$; $\partial Hy/\partial x$; $\partial Hy/\partial y$; $\partial Hy/\partial z$; $\partial Hz/\partial x$; $\partial Hz/\partial y$; and $\partial Hz/\partial z$.

14. The apparatus, as recited in claim 13, further comprising an actuating device for making the device for detecting the defect of the pipe to slide in uniform speed on the sliding track is provided.

15. The apparatus, as recited in claim 14, wherein the actuating device is controlled manually, or by air pressure or hydraulic pressure.

* * * * *